United States Patent [19]

Zamarripa et al.

[11] Patent Number: 4,781,962

[45] Date of Patent: Nov. 1, 1988

[54] COMPOSITE COVER MATERIAL FOR ABSORBENT ARTICLES AND THE LIKE

[75] Inventors: Isidro B. Zamarripa; Juna D. M. Tomas, both of Naucalpan, Mexico

[73] Assignee: Kimberly-Clark Corporation, Neenah, Wis.

[21] Appl. No.: 905,230

[22] Filed: Sep. 9, 1986

[51] Int. Cl.$^4$ .............................................. B32B 3/10
[52] U.S. Cl. ...................... 428/138; 428/137; 428/171; 428/172; 428/198; 428/284; 428/286; 428/296; 428/903; 428/913; 428/280; 428/282; 604/378; 604/379; 604/382
[58] Field of Search ............... 428/137, 138, 170, 171, 428/172, 198, 284, 286, 296, 68, 903, 913, 280, 282; 604/378, 379, 382

[56] References Cited

U.S. PATENT DOCUMENTS

| | | | |
|---|---|---|---|
| 3,331,728 | 7/1967 | Lane | 161/112 |
| 3,676,242 | 7/1972 | Prentice | 156/62.4 |
| 3,690,977 | 9/1972 | Loft et al. | 156/167 |
| 3,912,567 | 10/1975 | Schwartz | 428/296 |
| 3,949,127 | 4/1976 | Ostermeier et al. | 428/296 |
| 3,965,906 | 6/1976 | Karami | 128/287 |
| 3,967,623 | 7/1976 | Butterworth | 128/287 |
| 3,994,299 | 11/1976 | Karami | 128/287 |
| 4,014,341 | 3/1977 | Karami | 128/287 |
| 4,041,203 | 8/1977 | Broch et al. | 428/296 |
| 4,078,124 | 3/1978 | Prentice | 428/296 |
| 4,315,965 | 2/1982 | Mason et al. | 428/296 |
| 4,323,069 | 4/1982 | Ahr et al. | 128/287 |
| 4,324,247 | 4/1982 | Aziz | 128/287 |
| 4,333,979 | 6/1982 | Sciaraffa et al. | 428/296 |
| 4,374,888 | 2/1983 | Bornslaeger | 428/296 |
| 4,446,187 | 5/1984 | Eklund | 428/138 |
| 4,559,255 | 12/1985 | Shimode et al. | 428/138 |
| 4,588,630 | 5/1986 | Shimalla | 428/296 |
| 4,591,523 | 5/1986 | Thompson | 428/138 |
| 4,603,069 | 7/1986 | Hag et al. | 428/138 |
| 4,681,793 | 7/1987 | Linman et al. | 428/138 |

*Primary Examiner*—James J. Bell
*Attorney, Agent, or Firm*—Patrick C. Wilson

[57] ABSTRACT

A composite cover material for absorbent articles and the like and a method for making the same are disclosed herein. The cover material is made of a thermoplastic film in contact with an external layer of nonwoven material. Selective point application of heat and pressure to the external surface of the nonwoven material causes the formation of a plurality of densified and partially fused areas in the nonwoven which are in vertical alignment with a corresponding plurality of concurrently formed perforations in the film. The densified and fused areas in the nonwoven act to mask the perforations in the film and in addition, restrict fluid flow when the cover material is under compression by partially blocking the perforations in the film.

7 Claims, 2 Drawing Sheets

COMPOSITE COVER MATERIAL FOR ABSORBENT ARTICLES AND THE LIKE

BACKGROUND OF THE INVENTION

The present invention relates to a composite cover material which may be used by itself or in conjunction with absorbent articles and a process for making the same. More particularly, it relates to a cover material made of a perforated thermoplastic film with an external layer of fluid pervious nonwoven material having a plurality of locally densified and fused areas in vertical alignment with the perforations in the film. The densified and fused areas act to mask the perforations in the film. These same areas also act to partially block the perforations in the film when the cover material is compressed, thereby restricting fluid flow through the area under compression.

Most absorbent articles used in personal care products and other areas employ a cover material to contain and protect the absorbent material which is typically found in the interior of the product. Examples of such absorbent products include infant and adult diapers, medical bandaging and feminine sanitary products such as sanitary pads. The bulk of these products sold today are disposable, single use items. As a result, achieving maximum performance at a minimal cost is important in the design and acceptance of the product.

Acceptance of a product is not only dependent upon actual attributes but upon the user's perception of the product as well. For example, with feminine sanitary pads, not only must the product physically keep the user clean and dry, the user must perceive that the product is yielding these results. Otherwise the user will reject the product even though it is fulfilling its intended purpose.

Typically, absorbent articles include a bodyside cover, an absorbent interior and an external cover material or baffle to lessen or prevent leakage. In order to maximize performance of the absorbent article, the bodyside cover material must allow for the rapid transfer of fluid through itself and into the absorbent layer below. Once the fluid has been transferred to the absorbent layer, the cover material should present a clean and dry feel to the user. Nonwoven cover materials are frequently used in an attempt to achieve these properties. However, lightweight nonwovens, as are commonly used in such products, have poor masking capabilities and a limited ability to prevent rewetting once the fluid has been transferred to the absorbent layer. As a result, these cover materials may additionally employ a perforated film positioned between the nonwoven and the absorbent pad to form a two-piece cover material. To a certain degree, the film masks the absorbed fluid from the user's view and restricts backflow of fluid previously transferred to the absorbent layer. Examples of such materials can be found in U.S. Pat. Nos. 3,965,906, 3,994,299 and 4,014,341. However, given the relative number and size of holes that are needed to affect good fluid transfer into the absorbent layer, fluid flowback and masking are still a problem, especially in the case of menses with sanitary pads and urine with diapers.

It is, therefore, an object of the present invention to provide a cover material for absorbent articles and other uses which is comfortable while providing good masking characteristics.

It is another object of the present invention to provide a cover material with reduced fluid backflow or rewet when under compression.

These and other objects of the invention will become more apparent upon a further review of the accompanying specification, drawings and claims.

SUMMARY OF THE INVENTION

The present invention relates to a cover material and a method for making the same. The cover material may be incorporated into absorbent articles or used independently, as for example, in agricultural applications as a row cover or on fluid tanks to reduce evaporation. The cover material is comprised of a layer of thermoplastic film in contact with and bonded to an external layer of a fluid pervious nonwoven material which preferably has a higher melting point than the layer of thermoplastic film. The composite material is brought in contact with a pair of calender rollers. One of the rollers has a plurality of heated projections extending therefrom to contact the nonwoven side of the composite at localized points. Through the selective application of heat and pressure to the external surface of the nonwoven material, a plurality of densified and fused areas are formed in the nonwoven material which are in vertical alignment with a corresponding plurality of concurrently formed perforations in the thermoplastic film. The densified and partially fused areas of the nonwoven are more opaque than the remainder of the material. Given the vertical juxtaposition of the densified areas over the perforations in the film, the net effect is that the perforations tend to be hidden from view. Thus, when the present cover material is used in conjunction with an absorbent article such as a sanitary napkin, the densified areas act to mask from view the fluid trapped within the absorbent layer which would otherwise be more visible through the perforations in the film.

Again in the case of an absorbent article, when the present cover material is under little or no load, there is sufficient distance between the densified areas in the nonwoven material and the perforations in the film to permit fluid to pass through the nonwoven top layer and subsequently through the film and into the absorbent layer below. Upon compression or loading of the material, the densified and less pervious areas of the nonwoven are brought into closer contact with the perforations in the film, thereby restricting fluid flow through the perforations. Should select areas of the material be compressed during an insult by the user, as in the case of a sanitary napkin, the fluid will simply seek the nearest non-loaded area to penetrate into the absorbent layer. This movement of fluid into the absorbent layer is readily fostered by the fact that the nonwoven and the film are usually hydrophobic whereas the absorbent layer is generally quite hydrophilic. Once the insult has taken place, the chance of flowback under compression is reduced due to the blocking of the perforations by the densified areas in the nonwoven and the great disparity in fluid affinity between the hydrophilic absorbent layer and the hydrophobic cover material. As a result, the desirable clean and dry properties of the cover material are enhanced.

DESCRIPTION OF THE PREFERRED EMBODIMENT

Figure 1:
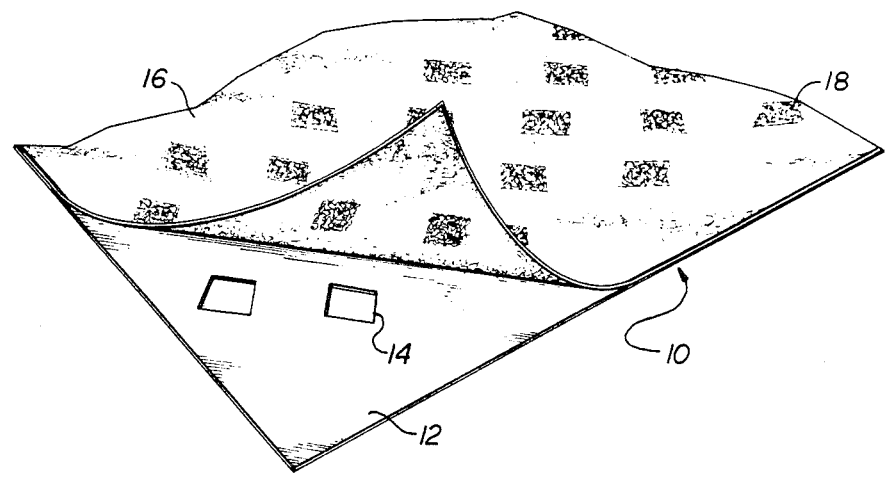
FIG. 1 is a perspective view of a composite cover material having a layer of nonwoven material fused to a layer of thermoplastic film according to the present invention.

Referring to FIG. 1 there is shown a composite cover material 10 according to the present invention. The cover material 10 includes a layer of fluid impervious material 12, such as a thermoplastic film which upon application of the present process has a plurality of perforations 14 formed therein. Examples of such materials include polyolefins and copolymers thereof. Two preferred polyolefins are polyethylene and polypropylene. The most important aspects of the film material 12 are that it be fluid impervious, preferably hydrophobic and have a melting point which is lower than the melting point of the nonwoven web material described below.

Figure 5:
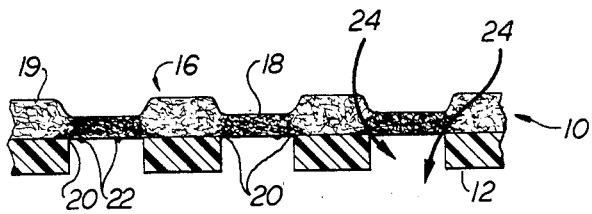
FIG. 5 is a side view of the material shown in FIG. 1. This is also a side view of the material as it would appear when the layers are under little or no compressive force.
Figure 6:
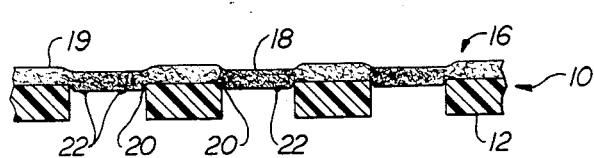
FIG. 6 is another side view of the material shown in FIG. 1. This time, however, the layers are shown while under compression.

On at least one side of the film layer 12 there is positioned a layer of liquid pervious nonwoven web material 16. As can be seen in FIGS. 1, 5 and 6 and as a result of the present process, the nonwoven web has a plurality of densified and fused areas 18 which directly overlie and are in vertical alignment with the perforations 14 in the film 12. As a result of the process of the present invention, the densified areas 18 are partially bonded to the peripheries of the perforations 14 in the film 12. These bond sites 20 are partial and therefore permit fluid to flow around the densified and fused areas 18 and then through the perforations 14 in the film layer 12.

The nonwoven web 16 may be a meltblown, spunbonded, carded web, bonded carded web, coform, airlaid or scrim reinforced material or a combination of the foregoing. As a result, the fibers of the nonwoven layer may be continuous, onon-continuous, staple fiber or a combination of such fibers. Furthermore, the fibers may be made from synthetic or natural components. Should the fibers be resistant to thermal bonding, a bonding additive such as a thermal adhesive may be added to the nonwoven web material to improve bonding. The types of fibers used and the method of forming the web will often depend upon the end use of the product. For personal care products such as diapers, napkins and bandages it is generally desirable to use a web that will be soft to the touch. For rugged uses such as agricultural row covers, a tougher more durable web would be desired.

Given the nature of the formation of the composite cover material 10, it is preferred that the nonwoven layer 16 have a higher melting point than that of the film layer 12. To create the densified and fused areas 18 in the nonwoven web 16, the web material must also be thermally bondable. In addition, the web material must have some degree of affinity for the film material so that bonding will occur when the two layers are subjected to heat and pressure. A preferred web material is a polypropylene carded web.

Figure 3:
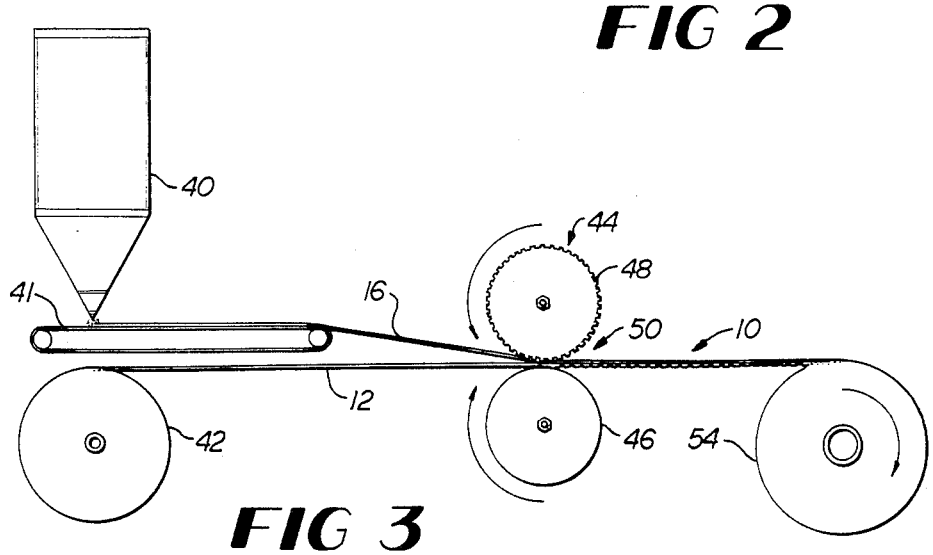
FIG. 3 is a diagrammatic view depicting the apparatus and process for making a cover material according to the present invention.

Turning to FIG. 3, there is shown a simplified diagrammatic view of the process for making a cover material 10 according to the present invention. A layer of nondensified, unbonded carded web material 16 is formed using conventional techniques and equipment well known to those skilled in the art. This equipment, including for example the card feeder and radomizer, is depicted by numeral 40 in FIG. 3. This web material 16 is laid down upon an endless forming belt 41 and directed to a pair of calendering rollers 44 and 46. At the same time, a roll 42 of unperforated thermoplastic film material 12 is unwound and fed toward the rollers 44 and 46. Referring to the enlarged view of the rollers in FIG. 4, the top or upper roller 44 has a plurality of projections 48 extending outwardly from its surface in a predetermined pattern for bonding purposes. As can be seen from the pattern of the perforations 14 and the fused and densified areas 18 in the cover material 16 of FIG. 1, the projections 48 are uniformly spaced and square shaped. It should be realized however that the shape of the projections is not critical so long as the desired bonding and percent open area are achieved. Consequently, any shape such as circles, rectangles, diamonds and polygons or a combination thereof maybe used to achieve the desired results. It is preferred that the pattern on the roller 44 create a percent open area in the film and a concurrent percent densified and fused area in the web of between 10 and 50 percent for each layer.

The bottom or lower roller 46 has a smooth surface. Together, rollers 44 and 46 define a nip area 50 wherein the cover material 10 is formed. The film 12 and the nonwoven web material 16 are fed into the nip area 50 such that the projections 48 contact the nonwoven side of the cover material 10. Consequently, the projections 48 on roller 44 must be sufficiently spaced and sufficiently deep so that the recesses 52 between the projections 48 do not permanently compress or unduly bond the non-densified areas 19 of the web 16. See FIG. 4. Otherwise the cover material 10 may not retain its soft feel which is important when the cover material is subsequently incorporated into personal care products.

Formation of the cover material 10 is a result of the heat and pressure supplied to the film 12 and the web 16 via rollers 44 and 46. Prior to entering the nip area 50, the film 12 is generally a continuous relatively uniform sheet without perforations and the web 16 is most typically of uniform density and thickness since the densified and fused areas 18 have not yet been formed into the web.

The heat necessary to form the cover material is supplied from one or both of the rollers 44 and 46. The top roller 44 with the projections 48 must be heated. Heat may be supplied by any number of means which are well know in the art, such as hot oil, steam, electrical resistance or gas flame. Heating of the smooth bottom roller 46 is optional but preferred.

The materials for the film 12 and the web 16 are chosen such that the web 16 has a higher melting point than the film 12. As a result, the heat and pressure of the projections 48 of roller 44 will densify and fuse the web 16 while completely perforating the thermoplastic film 12. To accomplish this, it is preferred that both rollers 44 and 46 be run at a temperature that is hotter than the melting point of the film 12 but less than the melting point of the web 16. Within this range it is also desirable to have the upper roller 44 a few degrees hotter than the smooth bottom roller 46. Furthermore, melting of the film onto the smooth roller 46 is avoided by keeping the dwell time of the materials on the heated rollers to a minimum and by using a doctor blade, if necessary.

As the cover material 10 moves through the nip area 50 between the rollers 44 and 46, the heated projections 48 form discrete areas of densification and fusion 18 in the locations where the projections 48 contact the surface of the nonwoven web 16. In the surrounding areas 19 of the nonwoven web 16, little or no compression takes place and as a result, this material remains basically unchanged.

At the same time that each of the projections 48 are forming the densified and fused areas 18 in the nonwoven web 16, the heat and pressure from the projections are also transferred through the nonwoven web 16 to the film 12. As a result of this heat and pressure transfer, the thermoplastic film melts and shrinks away from the heat source thus causing the film to open up and form the perforations 14. In addition, the heat and pressure of the projections 48 also cause individual pieces 22 of the melted film to transfer to at least a portion of the densified and fused areas 18 on the side of the nonwoven web 16 adjacent the film 12. (See FIG. 5.) These pieces of film 22 act to bolster the fluid impervious nature of the densified areas 18. They also act to improve the masking characteristics of the cover material by making the densified areas more opaque.

Besides simultaneously perforating the film and causing the nonwoven web to become densified and fused, the rollers 44 and 46 also cause a certain degree of bonding 20 between the film layer 12 and the nonwoven web layer 16 thereby making the cover a single-piece construction. As the fibers of the web 16 soften and the film melts, the pressure of the projections 48 against the materials causes a partial bonding of the web fibers about the periphery of the perforations in the film. It is this bonding which adds integrity to the overall cover material 10 so that it may act as a unitary structure. In between the perforations 14 and the densified areas 18 little or no bonding of the layers takes place. This is preferred in personal care applications since bonding of the layers lessens the softness of the nonwoven side of the cover material.

Once the cover material 10 has been formed, it can be rolled up into a roll 54 for later use as, for example, an agricultural row cover to aid in crop growth and production or for use as a tank cover to restrict the evaporation of fluids contained within the tank. Alternatively, the finished cover material 10 may be subject to further in-line processing or subsequent inclusion into an absorbent article such as a sanitary napkin, a diaper or a bandage.

It also should be understood that the process depicted in FIG. 3 is subject to certain modifications without departing from the spirit and scope of the present invention. Instead of forming the web material 16 in-line, it may be brought to the process in roll form and unwound and fed into the nip 50 of rollers 44 and 46 in the same fashion as the film roll 42. Conversely, the film 12 may be formed in-line as opposed to off-line. The critical aspect of the process is the simultaneous formation of the densified and fused areas in the web and the perforations in the film such that the densified areas and the perforations are in vertical alignment. Furthermore, the web should be bonded to the film about the peripheries of the perforations in the film. This is accomplished in the above-described manner by way of the rollers 44 and 46.

A cover material made according to the present invention has several advantages which make its use in a variety of areas quite beneficial. The first advantage is in the area of fluid flow. When a fluid such as water, urine or menses is directed toward the nonwoven web side 16 of the cover material 10, the fluid will readily flow through the web and toward the film 12. This is because the fibers of the web are usually hydrophobic and the pore size of the web in the non-densified areas 19 is rather large given the relatively low bulk density of the material which is typically in the range of 0.15 to 0.55 gm/cc. Thus the fluid will readily flow around and underneath the fluid impervious regions 18 of the web and then through the perforations 14 of the film 12. This fluid flow path is depicted by the arrows numbered 24 in FIG. 5.

Once the fluid has passed through the cover material 10, its travel in the reverse direction, from the film side to the nonwoven web side, is impeded first by the fluid impervious film 12 which will only permit fluid flow through the perforations 14. However, an additional imposition to fluid flow in the reverse direction is imparted to the material by the densified and fused areas 18 of the web 16 which directly overlie and are in vertical alignment with the perforations 14 in the film 12. This presents a particular advantage when the cover material is used as an agricultural row cover or an evaporation cover on tanks. This is because the material 10 will readily allow a liquid such as rain to pass through to the crops below while providing improved restriction of evaporation back through the cover material due to the fluid impervious areas 18 directly overlying the film perforations 14. At the same time, the cover material 10 will allow air circulation below the cover material thus making the material breathable. Consequently, the desired exchange of oxygen and carbon dioxide from photosynthesis can take place when the material is employed as an agricultural row cover.

The above-mentioned advantages of the present invention can be further utilized when the cover material 10 is incorporated into an absorbent article such as a sanitary napkin, diaper or bandage. Once such embodiment, a sanitary napkin, is shown in a cut-away view in FIG. 7.

Figure 7:
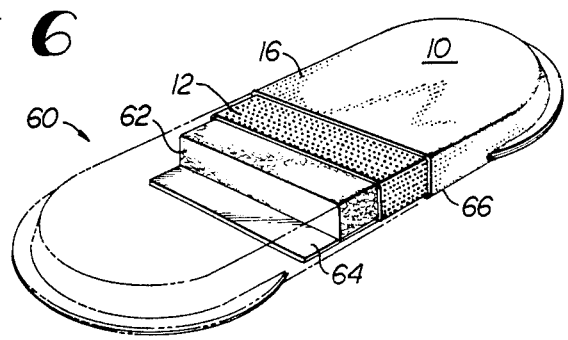
FIG. 7 is a perspective view with a partial cutaway showing an absorbent article, in this case a sanitary napkin, employing a cover material according to the present invention.

Referring to FIG. 7, there is shown a sanitary napkin 60 which employees a cover material 10, with the nonwoven web side 16 to the outside of the napkin. The film side 12 of the composite cover material 10 overlies an absorbent core 62 of fluff material such as, for example, ground wood pulp. The film 12 may be in direct contact with the absorbent core or it may be separated by one or more additional layers, as for example by a transfer layer. Directly underneath the absorbent core 62 and away from the bodyside of the product there may be optionally placed a secondary more densified layer of absorbent 64. The back side or baffle of the napkin 60 may be made of any suitable material known in the art such as a fluid impermeable film. Alternatively, the cover material 10 may be extended to cover the backside of the napkin 60.

When menses is directed toward the cover material 10 of the napkin 60, it will readily flow throught the web 16, down through the perforations 14 and then into the absorbent pad 62. Such flow is most easily achieved when the cover material 10 is under little or no compression, as is depicted in FIG. 5. When the cover material 10 is compressed, as is shown in FIG. 6, the densified and fused areas 18 of the nonwoven web 16 are brought into closer contact with the respective perforations 14 in the film 11. As a result, the amount of open area around the perforations 14 is reduced and the densified and fused areas 18 act to plug-up the perforations, thereby reducing fluid flow.

Should select areas of the cover material 10 be under compression during a further transfer of menses to the napkin 60, the menses that do not flow through the blocked perforations will enter the absorbent layer through areas of the cover material which are not under compression.

This regulation of fluid flow is particularly advantageous when the absorbent material is fairly loaded with fluid because it is the compression of the absorbent article which causes rewetting of backflow of fluid through the perforations and into the cover material. Without the densified and fused area 18 blocking the perforations 14 in the film 12, the fluid would readily flow back through the cover thereby causing rewet of the cover which is highly undesirable. Consequently, the cover material 10 of the present invention is useful in providing a cleaner and drier cover/product for the user.

An additional advantage of the present cover material lies in its improved masking ability. While a perforated film does much to mask a fluid, such as menses, contained within the underlying absorbent layer, the user can still view the menses through the perforations in the film. This is particularly true given the fact that the perforations in the film should provide from about 10 to about 50 percent open area to be effective in transferring fluid to the absorbent pad below. Given this degree of openness, a user can readily view the menses lying below the film. Covering the perforated film with a nonwoven material will improve masking to a small degree, however, for the most part such nonwoven materials are rather transparent. In contrast, the present cover material has the densified areas 18 directly overlying the perforations 14 in film material 12. Since the densified areas 18 are quite opaque, they act to mask or hide from view the fluid in the absorbent 62 which would otherwise be more noticeable. Consequently, the napkin has a cleaner appearance. This improvement is illustrated in FIG. 2 of the drawings.

Figure 2:
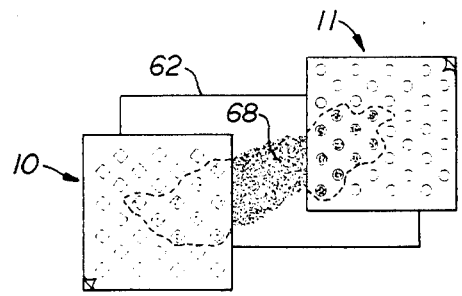
FIG. 2 is a top plan view of the masking ability of a cover material according to the present invention on the left as compared to a conventional cover material on the right.

Referring to FIG. 2, an absorbent material 62, similar to the absorbent core material in the sanitary napkin of FIG. 7, is shown with an area 68 stained with menses. On the left side of FIG. 2 there is shown a cover material 10 according to the present invention which overlies a portion of the stained area 68. On the right side of FIG. 7 there is shown a piece of cover material 11 which also overlies a portion of the stained area 68 and which comprises a perforated film covered by a nonwoven material. The materials of both covers 10 and 11 are identical except for the densified areas 18 in cover material 10 and the bonding between the layers, both of which are lacking in cover material 11. A visual comparison of the two cover materials demonstrates that the cover material 10 on the left is better at masking the menses contained within the absorbent pad 62 due to the densified area 18 overlying the perforations 14 in film 12. As a result, the cover material 10 according to the present invention, provides a more aesthetically appealing material.

EXAMPLES

As a comparison, the cover material of the present invention was incorporated into a sanitary napkin and evaluated against another sanitary napkin which employed a conventional nonwoven cover material. The results of the evaluation are shown in Table I. The first or conventional napkin used in the evaluation had an absorbent core made of wood pulp with a bulk density of 0.047 gm/cc. Directly below the absorbent material was another densified layer of the same absorbent having a bulk density of 0.054 gm/cc. The backside of the densified pad material of the napkin was covered with a layer of tissue followed by an exterior layer of plastic film to form the baffle. The bodyside cover of the conventional pad was a thermally bonded carded web of polypropylene which was in contact with the absorbent pad material. The polypropylene bonded carded web had a bulk density of 0.22 gm/cc.

The second sanitary napkin employing the cover material of the present invention was made by replacing the bodyside cover from one of the conventional pads described above. In its place there was provided a layer of the cover material 10 with the perforated film side 12 in contact with the absorbent pad. The cover material was made according to the process of the present invention as described hereinabove. The nonwoven web side of the cover material was a carded polypropylene web of 2.0 denier fibers having a bulk density of 0.22 gm/cc. The film was an extruded layer of polyethylene with perforations of 0.79 mm$^2$ uniformly spaced at 0.89 mm intervals to yield a 25 percent open area in the film. The percent open area is defined as the surface area of the total number of perforations divided by the total surface area of the film layer used, with the quotient being multiplied by 100.

Figure 4:
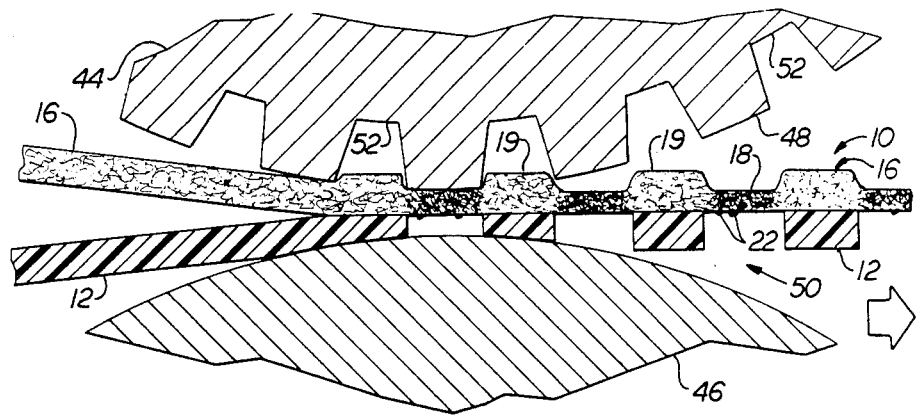
FIG. 4 is an enlarged cross-sectional view of the rollers shown in FIG. 3 used to make a composite cover material according to the present invention.

The film and web were run through a pair of heated calender rollers similar to those shown in FIGS. 3 and 4 of the drawings. The nonwoven web was adjacent the top roller with the projections. The top roller was heated to a temperature of 154° C. which was below the melting temperature of the polypropylene web 162° C. The smooth bottom roller was heated to a temperature of 151° C. which was below the temperature of the top roller and above the melting point of the polyethylene film 125° C. Spacing between the rollers was set such that the projections 48 were almost in contact with the smooth roller 46. With thicker materials the clearance between the rollers would be increased accordingly to prevent perforation of the web. As the film and web material passed through the nip area, the projections from the top roller acted in concert with the smooth bottom roller to form a plurality of densified and fused areas in the web while simultaneously forming a corresponding plurality of perforations in the film. Due to the heat and pressure of the rollers, the web was bonded to the film about the peripheries of the perforations which in turn meant that the densified areas of the web were in vertical alignment with the perforations in the film. The resultant cover material was then used as a cover over the conventional pad material and backing mentioned above.

The two sanitary napkins were tested and compared for a number of properties the first of which was the absorbency failure point in milliliters of fluid. The fluid used for the testing was a synthetic menstrual fluid comprising water thickened with arabic gum and red dye to a viscosity of 13.0 to 15.0 centipoise. Absorbency failure is defined as the point at which fluid leaks at the sides under manual side compression of the napkin. As can be seen in Table I, the conventional pad failed at a loading of 14.6 ml whereas the same pad with the present cover material was able to absorb 15.5 ml of fluid before failure.

TABLE I

|  | Sanitary napkin cover material construction | |
| --- | --- | --- |
|  | Conventional Polypropylene bonded carded web | Polypropylene bonded carded web/ perforated film |
| Lab absorbency/ failure (ml) | 14.6 | 15.5 |
| Absorbency rate (sec) for the first 4 ml of fluid (FC-10) | 37.0 | 83.0 |
| Rewet (gm) at 1.0 psi (FC-10) | 0.68 | 0.45 |
| Rewet (gm) at .50 psi (FC-10) | 0.58 | 0.36 |
| Rewet (gm) at 0.25 psi (FC-10) | 0.47 | 0.28 |
| Rewet (%) at 0.25 psi (Test Procedure II) | 12.7 | 2.3 |
| Cover stain area (cm$^2$)-A | 5.6 | 4.3 |
| Bottom fluff stain area (cm$^2$)-B | 25.1 | 27.8 |
| Fluid distribution ratio (B/A) | 4.8 | 6.2 |

The napkin with the conventional cover and the napkin with the cover material according to the present invention were next tested to determined the amount of rewet they would exhibit using the FC-10 International Rewet Test, Version 1, dated July 10, 1984 and a second test procedure outlined below. The only variation in the FC-10 test method was the use of synthetic menses instead of blood as the test fluid. The synthetic menses was formulated by thickening water with carboxymethylcellulose (CMC), glycerol, and red dye to yield a fluid having a viscosity of 15.8+/−1 centipoise.

As part of the FC-10 test procedure, the pads were subject to two separate insults of 4 ml each using the synthetic menses described above. Thus, the test also provided an indication of the absorbency rate of the two pads. As can be seen from Table I, the absorbency rate in seconds for the first 4 ml insult of fluid was 37.0 seconds and 83.0 seconds, respectively, for the pad with the conventional cover material and the pad with the cover material according to the present invention. The pad with the cover material of the present invention took longer to absorb the same amount of fluid. This is to be expected, however, considering the fact that the present cover material includes a perforated film with restricted open area disposed between the nonwoven and the absorbent, whereas; the conventional pad had a similar nonwoven in direct contact with the absorbent core. It should also be understood that the insult rates were much faster than would be encountered under normal use. Typically, an absorption rate below 120 seconds for the first 4 ml of fluid is considered adequate from the standpoint of feminine pad use. As a result, it can be seen that the pad with the present cover material is capable of performing the initial function of absorbing the menstrual fluid.

To calculate the rewet characteristics of the cover materials, the pads were first insulted with a predetermined quantity of fluid which has then allowed to absorb into the pads. The pads were then subject to a specified pressure for a predetermined time and the amount of fluid that flowed back through the cover was then measured. A desirable property of the material is that it limits the amount of fluid flowback or rewet.

Under the FC-10 procedure, each pad was loaded with a total of 8 ml of fluid during two separate 4 ml insults. Preweighed pieces of blotter material were then placed on top of the pads, in contact with the covers, and subjected to 1.0 psi of pressure for a period of three minutes. The pressure was then removed and the blotters were reweighed to measure the amount of fluid transmitted to and absorbed by the blotter. The amount of fluid absorbed was then calculated and this was in turn an indication of the amount of rewet exhibited by the particular cover material.

The results of the rewet testing, indicated as FC-10 Rewet Test in Table I, represent the average of ten separate tests run on ten samples each of a pad with a conventional cover and a pad with the cover material of the present invention. As can be seen from Table I, the conventional cover material at a pressure of 1.0 psi transferred an average of 0.68 grams of fluid to the blotter, whereas; the cover material of the present invention, under the same 1.0 psi pressure, only transferred an average of 0.45 grams of fluid to the blotter. This demonstrates that the present material provides better protection against rewet which translates into a drier cover material and resultant product.

The same FC-10 rewet test and numbers of samples were also run at 0.50 and 0.25 psi. The average of these results are also shown in Table I.

Again, the sanitary napkin with the cover according to the present invention provided better rewet protection and thus less transfer of fluid back to the surface of the cover when compared to the conventional cover material.

A second test (Test Procedure II) was also performed to determine the percent rewet of the two cover materials. Under the second test procedure, each pad was weighed before being insulted with a synthetic menstrual fluid made of water thickened with arabic gum and red dye to a viscosity of 13.0 to 15.0 centipoise. Each pad was then loaded with 5.5 ml of the fluid at a delivery rate of 5 ml/min. from a burette positioned just above the top surface of the pad. Upon absorption of the 5.5 ml of fluid, each pad was weighed and a weight was then placed on top of each pad, over the insult area, to simulate 0.25 psi of pressure. After five minutes, the weight was removed, a preweighed piece of blotter material was paced over the insult area of each pad and the weight was then reapplied to simulate 0.25 psi of pressure for two minutes. At the end of the two minutes, the weight was removed and the blotter material for each pad was reweighed. Once again, the amount of fluid absorbed by the blotter material was an indication of the amount of rewet exhibited by the cover material.

To calculate the percent rewet at 0.25 psi the net weight of the synthetic menstrual fluid contained in the blotter was divided by the weight of the synthetic menstrual fluid contained in the pad and the quotient was multiplied by 100 to give the percent rewet. The weight of the fluid in the pad was calculated by multiplying the original volume of fluid in the pad (5.5 ml) by the specific gravity of the fluid in gm/cc.

Referring to Table I, the percent rewet for the conventional napkin under Test Procedure II was 12.7 percent, whereas; the napkin with the present cover material had a rewet of 2.3 percent which is lower than the conventional cover/napkin by a factor of five. Thus, this data is an additional indication of the reduction in rewet resulting from the incorporation of the cover material of the present invention into an absorbent article such as a sanitary napkin. These same benefits can, in turn, be used to improve the rewet characteristics and thus the dryness of other absorbent articles such as diapers and bandaging.

In addition to the rewet calculations for each of the napkins, the cover stain area A for both types of napkins were also measured to further define the masking and rewet characteristics of the cover materials in conjunction with the pad constructions. To determine the stain area, 8 ml of the water/arabic gum synthetic menses described above was applied to each of the pads at a rate of 5.0 ml/min. Then, after a period of three minutes, the stain area in square centimeters was measured for the nonwoven cover portion of each of the pads. Referring to Table I, the napkin with the conventional nonwoven material had a stain area A of 5.2 $cm^2$ as compared to 4.5 $cm^2$ for the napkin using the present cover material. Thus, it can be seen that once the fluid was absorbed into the core, the napkin with the present cover material yielded a cleaner appearance. This also was visually perceivable since less fluid was present on the cover surface and the fluid below the perforated film was masked by both the opacity of the film and the densified areas in the nonwoven layer directly overlying the perforations in the film.

Next the stain area B on the lower layer of absorbent fluff adjacent the baffle was measured for each napkin. The stain on the bottom fluff of the conventional napkin was 25.7 $cm^2$. The stain on the bottom fluff of the napkin with the present cover material was 27.8 $cm^2$. This is an indication that more of the fluid was being transferred deeper into the absorbent core and away from the cover with the napkin using the cover material of the present invention. The degree of fluid transfer can also be viewed from the standpoint of the fluid distribution ratio which is the bottom fluff stain area B in $cm^2$ divided by the cover stain area A in $cm^2$. Here again, as can be seen from the data in Table I, the sanitary napkin with the present cover material provided a better fluid distribution as compared to the conventional cover material. It therefore becomes apparent that the cover material of the present invention when incorporated into an absorbent product such as a sanitary napkin provides an effective means for transferring fluids to the absorbent core while yielding a cleaner and drier surface with better masking and rewet characteristics.

Thus it can be seen that the present invention provides numerous advantages due to its construction and method of manufacture. While the invention has been described in connection with specific embodiments thereof, it is evident that many alternatives, modifications and variations of both the product and the process will be apparent to those skilled in the art in light of the foregoing description. In particular, although the cover material of the present invention has been described in connection with absorbent products and agricultural and industrial covers, other uses are clearly contemplated. Accordingly, it is intended to embrace all such applications, alternatives, modifications and variations as are within the spirit of the broad scope of the appended claims.

We claim:

1. A composite cover material comprising:
   a layer of thermoplastic film material having a plurality of fluid transmitting perforations extending therethrough, and
   a layer of fluid pervious nonwoven web material adjacent and bonded to one side of said perforated film, said nonwoven material further having discrete areas of densified and fused material in vertical alignment with said perforations in said thermoplastic film, whereby said area of densified and fused material act as a mask with respect to said film perforations and further act to restrict fluid flow through said perforations when said film and said nonwoven are compressed.

2. The cover material of claim 1 wherein said fluid pervious nonwoven material is hydrophobic.

3. The cover material of claim 1 wherein said nonwoven material has a higher melting point than the melting point of said film.

4. The cover material of claim 1 wherein said bonding between said film and said layer of nonwoven is primarily located about the perforations in said film.

5. The cover material of claim 1 wherein at least a portion of said areas of densified and fused nonwoven web material have individual pieces of thermoplastic film fused to a side of said areas adjacent said film to further aid in the masking and the restriction of fluid flow when said cover material is compressed.

6. A composite cover material comprising:
   a layer of thermoplastic film having a plurality of fluid transmitting perforations extending therethrough, and
   a layer of fluid pervious nonwoven web material adjacent and bonded to one side of said perforated film, said bonding between said perforated film and said layer of nonwoven being primarily located about the perforations in said film, said nonwoven material having a higher melting point than the melting point of said film, said nonwoven material having discrete areas of densified and fused material in vertical alignment with said perforations in said thermoplastic film and wherein at least a porton of said areas of densified and fused material have individual pieces of thermoplastic film fused to a side of said areas adjacent said film, whereby said areas act to mask said film perforations and further act to restrict fluid flow through said perforations when said film and nonwoven layers are compressed.

7. An absorbent article comprising:
   a cover material having a film of thermoplastic material with a plurality of fluid transmitting perforations extending therethrough and a layer of fluid pervious nonwoven web material adjacent and bonded to one side of said perforated film, said nonwoven material having discrete areas of densified and fused material in vertical alignment with said perforations in said thermoplastic film;
   a backing sheet; and
   an absorbent pad material disposed between said film of said cover material and said backing sheet.

* * * * *